United States Patent [19]
Studier et al.

[11] Patent Number: 5,766,905
[45] Date of Patent: Jun. 16, 1998

[54] CYTOPLASMIC BACTERIOPHAGE DISPLAY SYSTEM

[75] Inventors: F. William Studier, Stony Brook; Alan H. Rosenberg, Setauket, both of N.Y.

[73] Assignee: Associated Universities Inc., Washington, D.C.

[21] Appl. No.: 664,449

[22] Filed: Jun. 17, 1996

Related U.S. Application Data

[63] Continuation-in-part of Ser. No. 664,161, Jun. 14, 1996, abandoned.

[51] Int. Cl.$^6$ .............................. C12N 15/09; C12Q 1/70; A61K 39/00
[52] U.S. Cl. .................... 435/172.3; 435/235.1; 435/5; 935/58; 935/31; 424/184.1; 424/192.1
[58] Field of Search ............... 435/172.3, 5; 935/58, 935/31; 424/184.1, 192.1

[56] References Cited

U.S. PATENT DOCUMENTS

| | | | |
|---|---|---|---|
| 5,534,257 | 7/1996 | Mastico et al. | 424/192.1 |
| 5,550,035 | 8/1996 | Moss et al. | 435/69.1 |

OTHER PUBLICATIONS

Rosenberg and Studier, *The XIIIth International Conference on Virus and Bacteriophage Assembly* (1993).
Maruyama et al., *Proc. Natl. Acad. Sci. USA* 91: 8273–8277 (1994).
Sternberg and Hoess, *Proc. Natl. Acad. Sci. USA* 92: 1609–1613 (1995).
Rosenberg, A.H., et al., A Protein Display System Based on Bacteriophage T7, The 14th Biennial Conference on Phage/Virus Assembly. Held at Johnstown, Pennsylvania (1995).
Smith, G.P., and Scott, J.K., *Methods in Enzymology* 217: 228 (1993).
Smith, G.P., *Science* 228: 1315 (1985).
Parmley, S.F. and Smith, G.P., *Gene* 73: 305 (1988).
Scott, J.K. and Smith, G.P. *Science* 249: 386 (1990).
Cwirla, S.E., et al., *Proc. Natl. Acad. Sci. U.S.A.* 87: 6378 (1990).
O'Neil, K. T. and Hoess, R.H., *Current Opinion in Structural Biology*, 5: 443 (1995).
Smith, G.P. and Scott, J.K., *Methods in Enzymology*, 217: 228 (1993).
Lin et al. Biochemistry vol. 26, 1987, pp. 5267–5274.

*Primary Examiner*—Ponnathapura Achutamurthy
*Assistant Examiner*—Phuong T. Bui
*Attorney, Agent, or Firm*—Margaret C. Bogosian

[57] ABSTRACT

Disclosed are display vectors comprising DNA encoding a portion of a structural protein from a cytoplasmic bacteriophage, joined covalently to a protein or peptide of interest. Exemplified are display vectors wherein the structural protein is the T7 bacteriophage capsid protein. More specifically, in the exemplified display vectors the C-terminal amino acid residue of the portion of the capsid protein is joined to the N-terminal residue of the protein or peptide of interest. The portion of the T7 capsid protein exemplified comprises an N-terminal portion corresponding to form 10B of the T7 capsid protein. The display vectors are useful for high copy number display or lower copy number display (with larger fusion). Compositions of the type described herein are useful in connection with methods for producing a virus displaying a protein or peptide of interest.

18 Claims, 1 Drawing Sheet

5,766,905

SEQUENCE LISTING ( 1 ) GENERAL INFORMATION:

( i i i ) NUMBER OF SEQUENCES:70

( 2 ) INFORMATION FOR SEQ ID NO:1:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..54

( x i ) SEQUENCE DESCRIPTION: SEQ ID NO:1:

```
ATG CTC GGG GAT CCG AAT TCG AGC TCC GTC GAC AAG CTT GCG GCC GCA      48
Met Leu Gly Asp Pro Asn Ser Ser Ser Val Asp Lys Leu Ala Ala Ala
 1               5                  10                  15

CTC GAG TAACTAGTTA A                                                  65
Leu Glu
```

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Gly Asp Pro Asn Ser Ser Ser Val Asp Lys Leu Ala Ala Ala
 1               5                  10                  15

Leu Glu
```

( 2 ) INFORMATION FOR SEQ ID NO:3:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..60

( x i ) SEQUENCE DESCRIPTION: SEQ ID NO:3:

```
ATG CTC GGT GGA TCC GAT ATC GAA TTC GAG CTC CGT CGA CAA GCT TGC      48
Met Leu Gly Gly Ser Asp Ile Glu Phe Glu Leu Arg Arg Gln Ala Cys
 1               5                  10                  15

GGC CGC ACT CGA GTAACTAGTT AA                                        72
Gly Arg Thr Arg
             20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met Leu Gly Gly Ser Asp Ile Glu Phe Glu Leu Arg Arg Gln Ala Cys
1               5                   10                  15

Gly Arg Thr Arg
        20

( 2 ) INFORMATION FOR SEQ ID NO:5:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..60

( x i ) SEQUENCE DESCRIPTION: SEQ ID NO:5:

ATG CTC GGG GAT CCG ATA TCG AAT TCG AGC TCC GTC GAC AAG CTT GCG    48
Met Leu Gly Asp Pro Ile Ser Asn Ser Ser Ser Val Asp Lys Leu Ala
1               5                   10                  15

GCC GCA CTC GAG TAACTAGTTA A                                       71
Ala Ala Leu Glu
        20

( 2 ) INFORMATION FOR SEQ ID NO:6:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

Met Leu Gly Asp Pro Ile Ser Asn Ser Ser Ser Val Asp Lys Leu Ala
1               5                   10                  15

Ala Ala Leu Glu
        20

( 2 ) INFORMATION FOR SEQ ID NO:7:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..63

( x i ) SEQUENCE DESCRIPTION: SEQ ID NO:7:

ATG CTC GGG ATC CGA TAT CGA ATT CGA GCT CCG TCG ACA AGC TTG CGG    48
Met Leu Gly Ile Arg Tyr Arg Ile Arg Ala Pro Ser Thr Ser Leu Arg
1               5                   10                  15

CCG CAC TCG AGT AAC TAGTTAA                                        70
Pro His Ser Ser Asn
            20

( 2 ) INFORMATION FOR SEQ ID NO:8:

( i ) SEQUENCE CHARACTERISTICS:
　　　　( A ) LENGTH: 21 amino acids
　　　　( B ) TYPE: amino acid
　　　　( D ) TOPOLOGY: linear ( i i ) MOLECULE TYPE: protein ( x i ) SEQUENCE DESCRIPTION: SEQ ID NO:8:

Met Leu Gly Ile Arg Tyr Arg Ile Arg Ala Pro Ser Thr Ser Leu Arg
 1               5                  10                 15

Pro His Ser Ser Asn
            20

( 2 ) INFORMATION FOR SEQ ID NO:9:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:9:

TGAACTAGTA AATTC                                                     15

( 2 ) INFORMATION FOR SEQ ID NO:10:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:10:

AGCTTGCGGC CGCACTCGAG TAA                                            23

( 2 ) INFORMATION FOR SEQ ID NO:11:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:11:

CTAGTTACTC GAGTGCGGCC GCA                                            23

( 2 ) INFORMATION FOR SEQ ID NO:12:

( i ) SEQUENCE CHARACTERISTICS:
　　　　( A ) LENGTH: 14 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:12:

TAACTAGTAA ATTC                                                      14

( 2 ) INFORMATION FOR SEQ ID NO:13:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

ATAACTAGTT AACCCC                                                    16

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TAACTAGTTA ACCCC                                                     15

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CTAGATCTCA TTATCCA                                              17

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TATGGATAAT GAGAT                                                   15

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCTAGATCTC ATTATCATAT G                                   21

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:18:

TAACTAGATC TCATTATCAT ATG  23

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GGTGTGATGC TCGGGGATCC GAATTCGAGC  30

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GGTGTGATGC TCGGTGGATC CGATATCGAA TTCCG  35

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GCTCGGGGAT CCGATATCGA ATTCCG  26

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GGTGTGATGC TCGGGATCCG ATATCGAATT CCG  33

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
     CCGCTCTGCG GTAGG                                                              15
```

( 2 ) INFORMATION FOR SEQ ID NO:24:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
     GATCCGGCGA TTCGTGGCGA TACCTTTGCA TAAG                                         34
```

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
     AATTCTTATG CAAAGGTATC GCCACGAATC GCCG                                         34
```

( 2 ) INFORMATION FOR SEQ ID NO:26:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
     GATCCGAGCG CTTGGCGTCA CCCGCAGTTC GGTGGTTAAT G                                 41
```

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
     AATTCATTAA CCACCGAACT GCGGGTGACG CCAAGCGCTC G                                 41
```

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
     GATCTGGTTC CACGCGGCAG TGCGGATCCG ATATCG                                       36
```

( 2 ) INFORMATION FOR SEQ ID NO:29:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:29:

```
AATTCGATAT CGGATCCGCA CTGCCGCGTG GAACCA                                36
```

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..42

( x i ) SEQUENCE DESCRIPTION: SEQ ID NO:30:

```
ATG CTC GGG GAT CCG GCG ATT CGT GGC GAT ACC TTT GCA TAA                42
Met Leu Gly Asp Pro Ala Ile Arg Gly Asp Thr Phe Ala
 1               5                  10
```

( 2 ) INFORMATION FOR SEQ ID NO:31:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Met Leu Gly Asp Pro Ala Ile Arg Gly Asp Thr Phe Ala
 1               5                  10
```

( 2 ) INFORMATION FOR SEQ ID NO:32:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..48

( x i ) SEQUENCE DESCRIPTION: SEQ ID NO:32:

```
ATG CTC GGG GAT CCG AGC GCT TGG CGT CAC CCG CAG TTC GGT GGT TAA        48
Met Leu Gly Asp Pro Ser Ala Trp Arg His Pro Gln Phe Gly Gly
 1               5                  10                  15
```

( 2 ) INFORMATION FOR SEQ ID NO:33:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Met Leu Gly Asp Pro Ser Ala Trp Arg His Pro Gln Phe Gly Gly
 1               5                  10                  15
```

(2) INFORMATION FOR SEQ ID NO:34:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..54

(xi) SEQUENCE DESCRIPTION: SEQ ID NO:34:

```
ATG CTC GGG GAT CCG AGC CAG CCA GAA CTC GCC CCG GAA GAC CCC GAG    48
Met Leu Gly Asp Pro Ser Gln Pro Glu Leu Ala Pro Glu Asp Pro Glu
 1               5                  10                  15

GAT TAA                                                            54
Asp
```

(2) INFORMATION FOR SEQ ID NO:35:

(i) SEQUENCE CHARACTERISTICS:
    (A) LENGTH: 17 amino acids
    (B) TYPE: amino acid
    (D) TOPOLOGY: linear (ii) MOLECULE TYPE: protein (xi) SEQUENCE DESCRIPTION: SEQ ID NO:35:

```
Met Leu Gly Asp Pro Ser Gln Pro Glu Leu Ala Pro Glu Asp Pro Glu
 1               5                  10                  15

Asp
```

(2) INFORMATION FOR SEQ ID NO:36:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..87

(xi) SEQUENCE DESCRIPTION: SEQ ID NO:36:

```
ATG CTC GGG GAT CTG GTT CCA CGC GGC AGT GCG GAT CCG ATA TCG AAT    48
Met Leu Gly Asp Leu Val Pro Arg Gly Ser Ala Asp Pro Ile Ser Asn
 1               5                  10                  15

TCG AGC TCC GTC GAC AAG CTT GCG GCC GCA CTC GAG TAA                87
Ser Ser Ser Val Asp Lys Leu Ala Ala Ala Leu Glu
                20                  25
```

(2) INFORMATION FOR SEQ ID NO:37:

(i) SEQUENCE CHARACTERISTICS:
    (A) LENGTH: 28 amino acids
    (B) TYPE: amino acid
    (D) TOPOLOGY: linear (ii) MOLECULE TYPE: protein ( x i ) SEQUENCE DESCRIPTION: SEQ ID NO:37:

| Met | Leu | Gly | Asp | Leu | Val | Pro | Arg | Gly | Ser | Ala | Asp | Pro | Ile | Ser | Asn |
| 1 | | | | 5 | | | | | 10 | | | | | 15 | |

| Ser | Ser | Ser | Val | Asp | Lys | Leu | Ala | Ala | Ala | Leu | Glu |
| | | | 20 | | | | | 25 | | | |

( 2 ) INFORMATION FOR SEQ ID NO:38:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..129

( x i ) SEQUENCE DESCRIPTION: SEQ ID NO:38:

| ATG | CTC | GGG | GAT | CCG | AAT | TCG | AGC | TCC | GTC | GAC | AAG | CTT | GCG | GCC | GCA | 48 |
| Met | Leu | Gly | Asp | Pro | Asn | Ser | Ser | Ser | Val | Asp | Lys | Leu | Ala | Ala | Ala | |
| 1 | | | | 5 | | | | | 10 | | | | | 15 | | |

| CTC | GAG | ATC | AAA | CGG | GCT | AGC | CAG | CCA | GAA | CTC | GCC | CCG | GAA | GAC | CCC | 96 |
| Leu | Glu | Ile | Lys | Arg | Ala | Ser | Gln | Pro | Glu | Leu | Ala | Pro | Glu | Asp | Pro | |
| | | | 20 | | | | | 25 | | | | | 30 | | | |

| GAG | GAT | GTC | GAG | CAC | CAC | CAC | CAC | CAC | CAC | TGA | | | | | | 129 |
| Glu | Asp | Val | Glu | His | His | His | His | His | His | | | | | | | |
| | | | 35 | | | | | 40 | | | | | | | | |

( 2 ) INFORMATION FOR SEQ ID NO:39:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

| Met | Leu | Gly | Asp | Pro | Asn | Ser | Ser | Ser | Val | Asp | Lys | Leu | Ala | Ala | Ala |
| 1 | | | | 5 | | | | | 10 | | | | | 15 | |

| Leu | Glu | Ile | Lys | Arg | Ala | Ser | Gln | Pro | Glu | Leu | Ala | Pro | Glu | Asp | Pro |
| | | | 20 | | | | | 25 | | | | | 30 | | |

| Glu | Asp | Val | Glu | His | His | His | His | His | His |
| | | | 35 | | | | | 40 | |

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

GATCCGAATT CGCATATGTA A                          21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:41:

GATCCGAATT CGCATATGTA G    21

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GATCCGAATT CGCATATGTG A    21

(2) INFORMATION FOR SEQ ID NO:43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

GATCCGGAAT TCTAA    15

(2) INFORMATION FOR SEQ ID NO:44:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

GATCCCGTCT AA    12

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

GATCCGAATG CCGCAGCACT CGAGTAA    27

(2) INFORMATION FOR SEQ ID NO:46:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:46:

```
Glu  Ala  Ala  Gly  Ala  Val  Val  Phe  Lys  Val  Glu
 1                  5                      10
```

( 2 ) INFORMATION FOR SEQ ID NO:47:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

GAAGCTGCTG GTGCAGTGGT TTTCAAAGTG GAGTAATGCT G    41

( 2 ) INFORMATION FOR SEQ ID NO:48:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GAAGCTGCTG GTGCAGTGGT CTTTAAAGTG GAATAATGCT G    41

( 2 ) INFORMATION FOR SEQ ID NO:49:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Glu  Ala  Ala  Gly  Ala  Val  Val  Phe  Gln  Ser  Gly  Val  Met  Leu
 1                  5                      10
```

( 2 ) INFORMATION FOR SEQ ID NO:50:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

GAAGCTGCTG GTGCAGTGGT TTTTCAAAGT GGAGTAATGC TG    42

( 2 ) INFORMATION FOR SEQ ID NO:51:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

GAAGCTGCAG GAGCTGTCGT ATTCCAGTCA GGTGTGATGC TC    42

( 2 ) INFORMATION FOR SEQ ID NO:52:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:52:

CGCGGATCCA TATGGCTGAA TCTAATG     27

( 2 ) INFORMATION FOR SEQ ID NO:53:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:53:

GATTCGAACT TCTAAGCTAG CGAATTCCCG     30

( 2 ) INFORMATION FOR SEQ ID NO:54:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:54:

CTGCTGGTGC AGTGGTCTTT AAAGTGGAGT AACTAGTG     38

( 2 ) INFORMATION FOR SEQ ID NO:55:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:55:

AATTCACTAG TTACTCCACT TTAAAGACCA CTGCAGCACC AGCAGCTT     48

( 2 ) INFORMATION FOR SEQ ID NO:56:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:56:

CGAACTTCTA ACTAGTTAAC CC     22

( 2 ) INFORMATION FOR SEQ ID NO:57:

( i ) SEQUENCE CHARACTERISTICS:
      ( A ) LENGTH: 24 base pairs
      ( B ) TYPE: nucleic acid
      ( C ) STRANDEDNESS: single ( D ) TOPOLOGY: linear ( i i ) MOLECULE TYPE: DNA (genomic)

( x i ) SEQUENCE DESCRIPTION: SEQ ID NO:57:

CAAGGGGTTA ACTAGTTAGA AGTT                                                         24

( 2 ) INFORMATION FOR SEQ ID NO:58:

( i ) SEQUENCE CHARACTERISTICS:
                ( A ) LENGTH: 41 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:58:

CTGCAGGAGC TGTCGTATTC CAGTCAGGTG TGATGCTCGG G                                       41

( 2 ) INFORMATION FOR SEQ ID NO:59:

( i ) SEQUENCE CHARACTERISTICS:
                ( A ) LENGTH: 48 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:59:

GATCCCCGAG CATCACACCT GACTGGAATA CGACAGCTCC TGCAGCTT                                48

( 2 ) INFORMATION FOR SEQ ID NO:60:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:60:

CGGGATCCTC GGGGTGGCCT CAACG                                                        25

( 2 ) INFORMATION FOR SEQ ID NO:61:

( i ) SEQUENCE CHARACTERISTICS:
                ( A ) LENGTH: 38 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:61:

GGCTGCTGCC ACCGCGGAGC AATAACTAGT GAATTCGC                                          38

( 2 ) INFORMATION FOR SEQ ID NO:62:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:62:

```
GATCCGAGCC AGCCAGAACT CGCCCCGGAA GACCCCGAGG ATTAACTAGT G        51
```

( 2 ) INFORMATION FOR SEQ ID NO:63:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

```
AATTCACTAG TTAATCCTCG GGGTCTTCCG GGGCGAGTTC TGGCTGGCTC G        51
```

( 2 ) INFORMATION FOR SEQ ID NO:64:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

```
TGAACTAGTA AATTC                                               15
```

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

```
CTGCTGGTGC AGTGGTCTTT AAAGTGGAAT AAG                           33
```

( 2 ) INFORMATION FOR SEQ ID NO:66:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

```
AATTCTTATT CCACTTTAAA GACCACTGCA CCAGCAGCTT                    40
```

( 2 ) INFORMATION FOR SEQ ID NO:67:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

```
CGGGATCCAT ATGGCTGAGA AACGA                                    25
```

( 2 ) INFORMATION FOR SEQ ID NO:68:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:68:

CTCACTATAG GGAGACTAGT GAATTCGC                                        28

( 2 ) INFORMATION FOR SEQ ID NO:69:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:69:

CGCGGATCCA TATGGCTAAG AAGATT                                          26

( 2 ) INFORMATION FOR SEQ ID NO:70:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:70:

GACGGAGACT TCTAGAAGCT TCGGC                                          25

1

CYTOPLASMIC BACTERIOPHAGE DISPLAY SYSTEM

RELATED APPLICATIONS

This application is a continuation-in-part application of application Ser. No. 08/664,161 filed Jun. 14, 1996, now abandoned.

This invention was made with Government support under contract number DE-AC02-76CH00016, awarded by the U.S. Department of Energy. The Government has certain rights in the invention.

BACKGROUND OF THE INVENTION

Previous work has demonstrated that filamentous phage can be exploited for the construction of epitope libraries. In general, such efforts have involved the production of a "fusion phage" which is a filamentous virion displaying on its surface a foreign peptide fused to a coat protein, and harboring the gene for the fusion protein within its genome. Such libraries have been used, for example, to display random foreign peptides encoded by degenerate synthetic oligonucleotides spliced into the coat protein gene. Libraries produced in this manner can contain billions of peptide sequences. A phage which displays a peptide which is a ligand which binds with reasonably high affinity to another member of a specific binding pair (e.g., an antibody or other binding protein), also referred to as an affinity reagent. This affinity can be utilized in an affinity purification method to specifically remove the phage from the phage library. Such purified phages can be eluted without destroying their infectivity, and the peptide sequences which confer the specific binding property are easily identified by propagating the eluted phage in bacteria and sequencing the relevant region of the viral DNA.

Through the application of such techniques, billions of peptide epitopes can be screened in a high-throughput assay for the ability to bind specifically to an affinity reagent of interest. The capacity of this type of screening method vastly exceeds that of conventional expression systems in which the epitope is not displayed as part of the propagatable unit which encodes it.

SUMMARY OF THE INVENTION

The present invention relates, in one aspect, to a display vector comprising DNA encoding a portion of a structural protein from a cytoplasmic bacteriophage, joined covalently to a protein or peptide of interest. In preferred embodiments, the structural protein is selected from the group consisting of capsid, tail, tail-fiber and head-tail connector proteins. Exemplified are display vectors wherein the structural protein is the T7 bacteriophage capsid protein. More specifically, in the exemplified display vectors the C-terminal amino acid residue of the portion of the capsid protein is joined to the N-terminal residue of the protein or peptide of interest. The portion of the T7 capsid protein exemplified comprises an N-terminal portion corresponding to form 10B of the T7 capsid protein.

In preferred embodiments in which high copy number display is desired, wild-type T7 capsid protein regulatory signals are employed (e.g., promoter and translation initiation signals). Other embodiments which are useful for producing larger fusion at a lower copy number on the assembled viral capsid lack wild-type capsid protein promoter and translation initiation signals.

The subject invention also relates to cells containing a display vector of the type described above. Viral lysates

2 containing assembled cytoplasmic bacteriophage particles bearing fusions to a cytoplasmic structural protein are also encompassed.

Compositions of the type described above are useful in connection with methods for producing a virus displaying a protein or peptide of interest. In such methods, a virus-based display vector of the type described above is used to clone DNA fragments such that the display vector encodes a fusion protein comprising the portion of the structural protein fused to protein or peptide sequences encoded by the DNA fragments. Cells are then infected with the virus-based display vector and viral lysates are screened to identify viral particles in which the protein or peptide of interest is expressed as a fusion protein joined to the structural gene from the cytoplasmic bacteriophage.

DETAILED DESCRIPTION OF THE INVENTION

Figure 1:
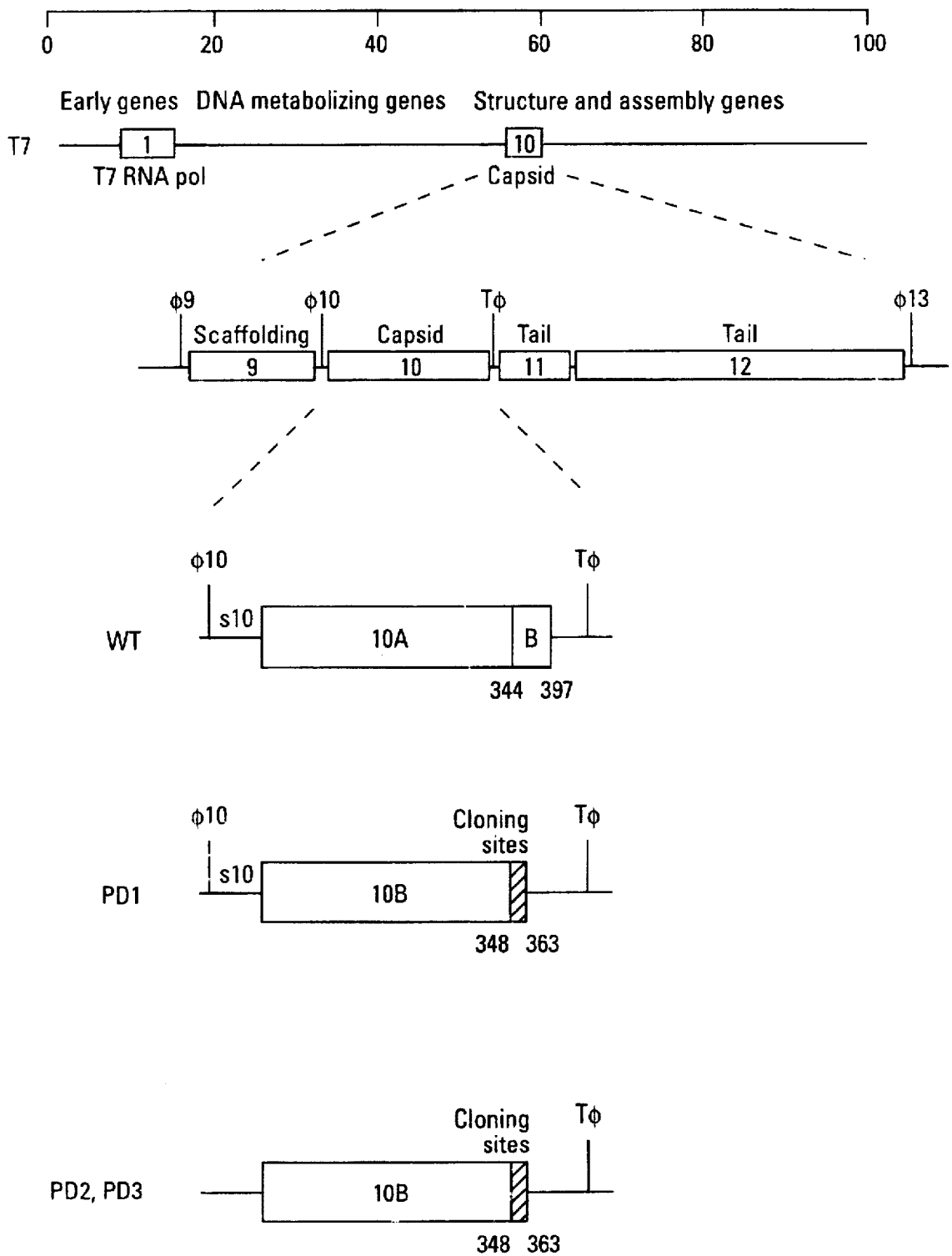
FIG. 1 is a diagrammatic representation of phage display constructs.

The present invention is based on the discovery that a cytoplasmic bacteriophage can be used to display proteins or peptides of interest, and that its use offers a number of advantages relative to previously employed techniques. More specifically, the present invention relates to the display of proteins or peptides as fusions to a structural protein from a cytoplasmic bacteriophage.

Cytoplasmic bacteriophage are assembled within the cell and released by cell lysis and include, for example, the T-phage (T1–T7) and related phage, lambdoid phage (e.g., lambda and P22), φ29, P1 and P2. The genome of members of the cytoplasmic bacteriophage family has a number of structural genes which encode proteins which are partially exposed in the assembled viral particles. Such structural genes include, for example, capsid, tail, tail-fiber and head-tail connector genes.

The subject application is based on the previously unproven hypothesis that it may be possible to construct a fusion protein comprising all, or a portion of one of the cytoplasmic bacteriophage structural proteins, fused to a protein or peptide of interest, without significantly affecting the ability of the fusion protein to participate in the assembly of a viral particle of substantially uncompromised integrity. In addition to the requirement that fusion of a protein or peptide of interest to the structural protein should not substantially affect its participation in viral particle assembly, a further requirement is that in the assembled viral particle, the protein or peptide of interest (or a portion thereof) must be exposed on the surface of the assembled viral particle and able to interact with other biological molecules. This requirement is essential for affinity screening or selection (e.g., using an affinity reagent such as a monoclonal antibody to identify phage particles containing a fusion which includes the protein or peptide of interest).

As a general proposition, there is no reason to assume, a priori, that fusion of the protein or peptide of interest to the N-terminus of the structural protein should yield better display results than fusion to the C-terminus (the converse is also true). However, for a particular structural protein, there may be considerations which dictate that, for example, fusion of the protein or peptide of interest to the C-terminus of the structural protein are favored over fusion to the N-terminus.

In the initial experiments described in detail below, the T7 bacteriophage capsid protein was the selected structural protein. The capsid protein of bacteriophage T7 is normally made in two forms, 10A (344 amino acids) and 10B (397 amino acids), related by a well-defined translational frameshift at amino acid position 341 (Condron et al., *J. Bacteriol.* 173: 6998 (1991)). 10B is completely dispensable, which suggested that the C-terminus of 10B might be useful for phage display.

In the experiments described below, a variety of fusion constructs were made in which protein or peptide sequences were fused at, or near, amino acid 348 of 10B, near the beginning of the region of amino acids unique to 10B. The natural translational frame shift site at amino acid 341 has been removed, so the capsid fusion gene is in a single reading frame coding for only one form of capsid fusion protein. Such fusions were determined to participate in viral particle assembly, and the non-capsid protein portion of such fusion proteins were positioned on the outer surface of the viral particle, accessible for interaction with other proteins.

Use of the fusion site at 10B amino acid 348 is not meant to indicate that this is the only position useful for phage display. Routine experimentation may reveal that additional residues of the 10B protein may be removed or included without compromising the ability of capsid fusion to participate in viral particle assembly. Removing more than a few amino acids from the C-terminus of the 10A protein appears to inactivate the protein, and probably indicates a limitation for the N-terminal-most position of the fusion site.

Thus, in one aspect, the present invention relates to display vectors containing DNA encoding a portion of a structural protein from a cytoplasmic bacteriophage, joined covalently to a protein or peptide of interest. In preferred embodiments, display vector is generated using the cytoplasmic bacteriophage genome as the starting material. Such vectors are referred to herein as "virus-based" display vectors. In general, such display vectors are generated by deleting non-essential DNA sequences such that the display vector, containing exogenous insert DNA, can be efficiently packaged within the viral particle.

In addition to the deletion of non-essential sequences, other alterations are generally made for matters of convenience. For example, as alluded to above, a linker containing a multiple cloning site can be inserted at a location in the viral genome which encodes the structural protein to which the protein or peptide of interest is to be fused. Furthermore, the 10B coding sequence on both sides of the position of the natural translational frame shift was altered without changing the encoded amino acids. This was done to minimize possible homologous recombination between a viral capsid gene and a plasmid-encoded capsid gene when in the same cell.

In the embodiment exemplified below, the protein or peptide of interest was fused to amino acid 348 of 10B. A number of variations of this general fusion strategy were employed. For example, in a first variation (referred to in the Exemplification section as PD1), peptides of up to about 40–50 amino acid residues can be expressed in high copy number on the surface of an assembled T7 viral particle. More specifically, the T7 is an icosahedral phage and has 415 copies of capsid protein per phage. In the PD1 display vector, wild-type promoter (i.e., φ10 promoter) and translation initiation signal (s10 translation initiation signal) were retained. The wild-type regulatory signals drive expression of capsid protein during PD1 infection at levels which approximate capsid protein expression during infection by wild-type T7. PD1 and the other vectors described below contained deletions (D104 and Δ3.8) that remove about 2700 base pairs of inessential DNA thereby accommodating DNA encoding a protein of about 900 amino acids.

PD1 was grown on the BL21 strain of *E. coli*, a B-strain that lacks the B restriction system. Alternatively, most *E. coli* strains lacking B or K restriction systems could be used. In this strain of *E. coli*, PD1 is the only source of viral capsid protein. Therefore, the copy number of the capsid/peptide fusion proteins displayed from PD1 is assumed to be 415. As indicated in the Exemplification section which follows, there was no evidence of any truncated protein assembled into capsids in gel analysis of phage structural proteins.

PD2 (and reading frame variants PD2a, PD2b and PD2c) and PD3, which are also virus-based display vectors, can be used to display larger proteins as a fusion to amino acid 348 of 10B. PD2 and PD3 differ from PD1 in that the wild-type translation initiation and promoter sequences for the capsid gene were deleted. This modification results in a substantial reduction in the synthesis of the capsid fusion protein. Thus, the virus-based PD2 display vector must be grown in a host providing an additional source of viral capsid protein. For example, a plasmid containing an expressible copy of the T7 capsid protein capable of participating fully in viral particle assembly can be introduced into a suitable *E. coli* strain in advance of infection by PD2. The low level of capsid protein fusion expression from PD2 results in the incorporation of the fusion protein at low copy number (e.g., 1 or slightly fewer copies per assembled phage) relative to the capsid protein provided from a separate source (e.g., a resident plasmid).

A third virus-based display vector is also specifically disclosed in the Exemplification section which follows. The PD3 display vector was produced by effectively deleting additional sequence from the PD2 display vector. More specifically, deletion of T7 genes 4.2 to 4.7 was effected in the manner described below, thereby increasing the cloning capacity to about 1,200 amino acids. The products of these deleted genes are nonessential for T7 growth on normal laboratory hosts. The PD3 display vector shares most of the characteristics of PD2. It can be used to display larger protein sequences as a fusion to the 10B form of the T7 capsid protein in low copy number, and it must be grown in a host which provides an additional source of capsid protein (e.g., from a resident plasmid).

In practice, the display vectors of the present invention can be used, for example, to screen or select for virus bearing a capsid fusion protein which contains, as an element of the fusion protein, a protein or peptide of interest. Such vectors find application, for example, in the expression screening of a DNA library in an effort to identify a protein or peptide having particular binding characteristics. Such binding characteristics include, for example, the ability to bind to a predetermined protein of interest (e.g., a regulatory protein or antibody) or DNA of interest.

In such an application, randomly generated DNA fragments of interest (e.g., fragments from a cDNA library) are cloned into the virus-based display vector to produce a library. This library is then used to infect a suitable host. If necessary (as is the case with PD2 and PD3) the host will contain a resident plasmid encoding the T7 capsid protein.

The life cycle of the lytic, cytoplasmic bacteriophages lead ultimately to the lysis of their host cell and the release of assembled viral particles. A common laboratory technique for phage screening is to plate packaged phage on a lawn of host cells at an appropriate phage dilution to produce a suitable number of plaques (an area of lysed cells on a lawn of cell growth) per plate to facilitate efficient screening.

Virus from the plaques can be transferred directly to a membrane (e.g., nitrocellulose) and screened using an affinity reagent such as an antibody. Specific binding of the affinity reagent can be detected by conventional techniques. This technique is commonly referred to as a "plaque Western blot".

Antibody binding to a portion of the blot corresponding to a particular plaque identifies the plaque as the source of viral particles displaying the protein or peptide of interest on its surface. By propagating the virus from the plaque identified in this manner, it is a straight forward matter to isolate DNA encoding the protein or peptide of interest. This DNA can be further characterized, for example, by DNA sequencing and/or expression within another context.

In a variation of the display screening embodiment described above, DNA encoding substantially similar fragments can be cloned into the display vector and binding techniques can be employed to identify subtle differences in binding affinity. For example, DNA encoding a protein or peptide of interest, which is known to bind to a particular regulatory protein, can be altered by conventional techniques to create a large number of variants (e.g., up to about $10^8$–$10^9$). The DNA is cloned in the display vector and the phage that bind most strongly to a target can be selected from a lysate using established biopanning techniques. The phage display has been used to identify peptides that bind to a wide variety of targets, including proteases, receptors, antibodies and DNA; to create diverse libraries of antibodies; to select and study DNA binding proteins; and to obtain proteins with altered enzymatic characteristics (O'Neil and Hoess, Curr. Opinion in Struct. Biol. 5: 443 (1995)).

EXEMPLIFICATION

Table 1 below summarizes the characteristics of T7 phage display vectors PD1, PD2 and PD3. The PD2 vector was modified to facilitate cloning in all 3 reading frames (PD2a, PD2b and PD2c). In each of the display vectors, the bacteriophage T7 capsid gene was employed as the structural gene to which a protein or peptide of interest was fused. More specifically, the display vectors encode amino acids 1–348 of the 10B form of the T7 capsid, followed by a series of cloning sites (see following text and FIG. 1). The 10B protein in wild-type T7 is made by a translational frameshift, but the 10B fusion gene in these vectors is in a single frame. The PD1 capsid gene has wild-type control signals: φ10 promoter, Tφ terminator, s10 translation initiation signals.

φ10 and s10 were removed from PD2 and PD3 to reduce capsid gene expression.

TABLE 1

| | T7 Phage Display Vectors | | | |
|---|---|---|---|---|
| Vector | Use | Copy # | Limitations | Host |
| PD1 | Peptides | 415 | 40–50 aa | BL21 |
| PD2 | Peptides or proteins | 0.1–1 | 900 aa | BL21/pAR5403 |
| PD2a | " | " | " | " |
| PD2b | " | " | " | " |
| PD2c | " | " | " | " |
| PD3 | Peptides or proteins | 0.1–1 | 1200 aa | BL21/pAR5403 |

The T7 capsid shell contains 415 copies of capsid protein, and the PD1 clones display 415 copies of peptide per phage when grown, for example, on host BL21, where the phage is the only source of capsid protein. The copy number of peptides or proteins displayed from PD2 or PD3 vectors is an expected copy number based on measurements of 4 different proteins displayed from PD2.

As discussed in greater detail below, peptides of up to 39 amino acids have been displayed from PD1, although the upper limit is likely somewhat higher. Selected inessential DNA was removed from PD1 to make PD2. PD2 vectors have sufficient space for cloning a 900 aa protein. Additional inessential DNA was removed from PD3 to increase the capacity to 1200 aa. For comparative purposes, the sizes of the display vectors are: PD1, 37,314 bp; PD2, 37,238 bp; PD2a, 37,245 bp; PD2b, 37,244 bp; PD2c, 37,243 bp; PD3, 36,219 bp. Wild-type bacteriophage T7 is 39,937 bp.

The host listed in Table 1 is for growth of the vector phage and of most clones. As discussed elsewhere, a variety of alternatives are available. Any specific modifications required are described herein and their construction is within the skill of the art. PD2 and PD3 phage produce only small amounts of capsid protein, and must be grown on a complementing host, such as BL21/pAR5403. This host supplies the 10A capsid protein under T7 promoter control. PD2 and PD3 clones that grow poorly on BL21/pAR5403 usually grow better on BL26/pAR5615, where the 10A protein is controlled by the lacUV5 promoter.

The specific cloning sites introduced following amino acid 348 of the 10B form of the T7 bacteriophage capsid protein are shown immediately below. The specific linkers used to introduce these sites into particular vectors are also shown.

```
10B------------ BamHI EcoRI SacI SalI HindIII NotI XhoI
aa 1         348                                   363
```

PD1, PD2, PD3 Cloning Site

-continued

```
     348                                                     363
Met Leu Gly Asp Pro Asn Ser Ser Ser Val Asp Lys Leu Ala Ala Ala Leu Glu
ATG CTC GGG GAT CCG AAT TCG AGC TCC GTC GAC AAG CTT GCG GCC GCA CTC GAG
            BamHI    EcoRI   SacI    SalI HindIII  NotI         XhoI

TAACTAGTTAA
```

PD2a Cloning Site

```
     348
Met Leu Gly Gly Ser Asp Ile Glu Phe Glu Leu Arg Arg Gln Ala Cys Gly Arg
ATG CTC GGT GGA TCC GAT ATC GAA TTC GAG CTC CGT CGA CAA GCT TGC GGC CGC
            BamHI   EcoRV   EcoRI    SacI    SalI HindIII  NotI 368
Thr Arg Val Thr Ser
ACT CGA GTA ACT AGT TAA
   XhoI
```

PD2b Cloning Site

```
     348
Met Leu Gly Asp Pro Ile Ser Asn Ser Ser Ser Val Asp Lys Leu Ala Ala
ATG CTC GGG GAT CCG ATA TCG AAT TCG AGC TCC GTC GAC AAG CTT GCG GCC
            BamHI   EcoRV   EcoRI    SacI    SalI HindIII  NotI 365
Ala Leu Glu
GCA CTC GAG TAACTAGTTAA
           XhoI
```

PD2c Cloning Site

```
     348
Met Leu Gly Ile Arg Tyr Arg Ile Arg Ala Pro Ser Thr Ser Leu Arg Pro
ATG CTC GGG ATC CGA TAT CGA ATT CGA GCT CCG TCG ACA AGC TTG CGG CCG
            BamHI   EcoRV   EcoRI    SacI    SalI HindIII  NotI 366
His Ser Ser Asn
CAC TCG AGT AAC TAGTTAA
       XhoI
```

In the construction of the display vectors, the capsid gene was first constructed in a plasmid and then transferred into phage by homologous recombination. For example, in constructing the PD1 display vector, a double stranded oligonucleotide (shown below) was inserted between the HindIII and SpeI sites of pAR5266 to remove the HSV epitope-His tag and to insert and re-establish the polylinker and 2 terminators, creating pAR5396.

the sequence upstream of 10B through the natural gene 9 sequence and adds the third terminator and the Tφ sequence downstream of the polylinker, creating pAR5402.

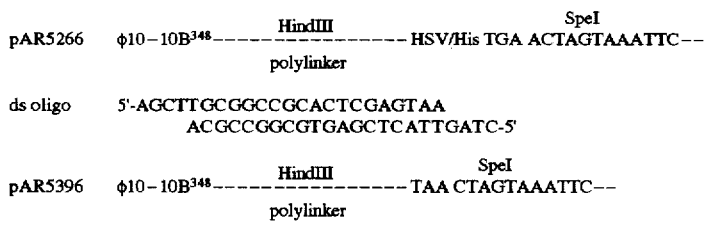

The Acc65I-SpeI fragment of pAR5129 was replaced with the Acc65I-SpeI fragment of pAR5396, which extends

```
                       Acc65I      SpeI
pAR5129   φ9-9-φ10-10A-TAA CTAGTTAACCCC-Tφ--
```

-continued

```
                Acc65I                          SpeI
pAR5402:    φ9-9-φ10-10B³⁴⁸--------------TAA CTAGTTAACCCC-Tφ--
                                 polylinker
```

PD1 was made by homologous recombination between T7-D104,Δ3.8,Δφ10-10AB and pAR5402. A lysate of T7-D104,Δ3.8,Δφ10-10AB was grown on HMS174/pAR5402 and plated on BL21. Only phage that carry the capsid gene can grow. A PD1 candidate was sequenced across the polylinker and through the Tφ and into the T7 sequence provided from the infecting phage to verify that the sequence was as expected.

The PD2 capsid gene was first constructed in a plasmid and then transferred into phage by homologous recombination. The translation initiation site (s10) upstream of the capsid gene ATG was removed by replacing the XbaI-NdeI fragment of pAR5135 with a double stranded oligonucleotide that also introduced a BglII site, creating pAR5365.

```
                  XbaI       NdeI
pAR5135    φ10-------s10---ATG---10B---

BglII
ds oligo   5'-CTAGATCTCATTATCCA
              TAGAGTAATAGGTAT-5'

XbaI            NdeI
pAR5365    φ10--TCTAGATCTCATTATCATATG--10B
```

The φ10 signal was removed and an appropriate plasmid created to make PD2 by homologous recombination by replacing the SpeI-EcoRI fragment of pAR5120 with the XbaI-EcoRI fragment of pAR5365, creating pAR5426.

```
              SpeI    EcoRI
pAR5120    φ9-9------Tφ-----

Spe/Xba                        EcoRI
pAR5426    φ9-9----TAACTAGATCTCATTATCATATG---10B-------
```

PD2 was made by homologous recombination between PD1 and pAR5426. A lysate of PD1 was grown on HMS174/pAR5426 and plated on BL21/pAR5403, a 10A complementing strain where both PD1 and recombinants that lack the capsid gene control signals (PD2 candidates) will grow. PD2 candidates were obtaining by screening plaques by spot tests on both BL21 and BL21/pAR5403. PD2 was designed to make little or no capsid protein and, therefore, does not grow on BL21. A PD2 candidate was sequenced across the capsid gene control region and across the polylinker to verify that the sequence was as expected.

The three different reading frame vectors were made by cloning PCR DNAs between the unique BssHII and EcoRI sites of PD2. The template for the PCR reaction was PD1 and the downstream PCR primer introduced the reading frame and an additional EcoRV site in the polylinker. The PCR DNA was made, cut with BssHII and EcoRI, and cloned in PD2 cut with the same enzymes. Plaques were screened in batches of 10 by making a PCR DNA that included the polylinker sequence and cutting with EcoRV. Plaques from positives were then screened individually in the same way. PD2a, PD2b, and PD2c candidates were sequenced across the polylinker to verify that they contained the expected sequence.

```
                                              348
PD1      10B-----GGT GTG ATG CTC GGG GAT CCG AAT TCG AGC ---
                                         BamHI        EcoRI

Complement of the downstream primers:

PD2a     5'-GGT GTG ATG CTC GG/T GGA TCC GAT ATC GAA TTC CG
                              BamHI     EcoRV     EcoRI

PD2b               5'-G CTC GGG GAT CCG/ ATA TCG AAT TCC G
                              BamHI     EcoRV    EcoRI

PD2c     5'-GGT GTG ATG CTC GGG/ ATC CGA TAT CGA ATT CCG
                              BamHI    EcoRV     EcoRI

Upstream primer:  5'-CCGCTCTGCGGTAGG   5' nucleotide is nuc 23,848 of WT T7
```

PD3 was made by ligating appropriate fragments of T7-HS33 (Δ13,278–14,296) and PD2, followed by packaging and screening. The HS33 deletion removes genes 4.2 to 4.7, all inessential for T7 growth on normal laboratory hosts. The left-most XbaI fragment (containing the D104 and Δ3.8 deletions) and the right-most BstEII fragment of PD2 (containing the PD2 capsid gene) were ligated together with the XbaI-BstEII fragment of HS33 containing the HS33 deletion, packaged, and plated on BL21/pAR5403. Plaques were screened for the HS33 deletion by PCR in batches of 10, and individual plaques from a positive were then screened. PD3 candidates were screened by restriction analysis for the presence of the PD2 capsid gene and deletions D104, Δ3.8, and HS33. The phage DNA was sequenced across the HS33 deletion to determine the endpoints of that deletion.

All phage display vectors contain deletions D104 (Δ579–2,746) and Δ3.8 (Δ11,163–11,515). D104 deletes genes 0.3 and 0.7 and Δ3.8 deletes gene 3.8. 0.7 and 3.8 are inessential on normal laboratory hosts; 0.3 is inessential on hosts that lack B and K restriction systems. Summarized in Table 2 below is the construction of phage representing precursors to the phage display vectors.

TABLE 2

Display Vector Precursors

| | |
|---|---|
| D104 | Deletion mutant (Δ579-2746) was selected by heat treatment of a wild-type lysate, grown on BL21, and analyzed by restriction of DNA from purified phage (Studier, J. Mol. Biol. 79:237 (1973)). |
| Δ3.8 | Deletion mutant (Δ11, 163-11, 515) was made by homologous recombination with pAR5070, grown on BL21, and sequenced across the deletion (Rosenberg et al., J. Biol. Chem. 267: 15005 (1992)). |
| D104, Δ3.8 | D104, Δ3.8 was made by co-infection of BL21, grown on BL21, and analyzed by restriction. |
| Δϕ10-10AB | Δϕ10-10AB was made by homologous recombination between WT and pAR5120, heat enriched for deletions, grown on BL21/10A-5116, screened by spot tests on BL21 and BL21/10A-5116, and analyzed by restriction. |
| D104, Δ3.8, Δϕ10-10AB | D104, Δ3.8, Δϕ10-10AB was made by co-infection of BL21/10A-5116, heat enriched, grown on BL21/10A-5116, screened for capsid gene deletion by spot tests, and screened by restriction. |

For packaging, PDpkg (=D104,Δ3.8,Δ9-10AB) was made by homologous recombination between D104,Δ3.8 and pAR5452. A heated lysate was plated on BL21/9-3924,10A-5453, where all phage should grow, and spot-tested for the 9-10AB deletion on BL21/9,10 and BL21. The DNA of deletion candidates was analyzed by restriction for all 3 deletions.

Wild-type T7 grows well on many *E. coli* strains, but does not grow on most male (F plasmid) strains. The first protein made during T7 infection, the 0.3 protein, is an anti-restriction protein that enables the phage to grow on cells that have B or K restriction systems. The phage display vectors lack the 0.3 gene, and must be grown on cells that lack these systems. BL21 (F⁻ ompT r⁻$_B$m⁻$_B$) is a standard non-restricting T7 host. BL26 is a lac deletion derivative (argF-lac) of BL21.

PD1 phage make normal amounts of capsid protein, and grow well on BL21. PD2 and PD3 make only small amounts of capsid protein, and must be grown on a complementing host. BL21/pAR5403 is a plasmid strain that produces large amounts of 10A capsid protein after infection by T7. Growth of PD1 phage on BL21/pAR5403 will yield phage that have capsids made up of a mixture of 10A and fusion capsid proteins.

BL21/pAR5403 is somewhat inhibitory to T7 growth, perhaps because it produces too much capsid protein. Plaques are smaller, but lysate titers seem little affected. A less inhibitory host, BL26/pAR5615, has been recently made where 10A expression is controlled by a lacUV5 promoter. Several examples were demonstrated of phage displaying larger proteins (>600 amino acids) that gave tiny plaques on BL21/pAR5403 and accumulated deletions in the capsid fusion gene. These phage gave larger plaques on BL26/pAR5615, and produced lysates without detectable deletion phage. BL26/pAR5615 may also be a useful host for making PD2 and PD3 libraries.

Growth of PD2 or PD3 clones on BL26/pAR5615 requires the addition of IPTG to induce production of the 10A protein. IPTG was generally added to 1 mM about ½ hr before infection to make lysates. For plating, 100 μl IPTG (0.1M) was added to 2.5 ml top agar before plating (25 ml agar plates).

TABLE 3

Selected Plasmids

| Plasmid | Parent | Antibiotic Resistance | Cloned Gene | Promoter |
|---|---|---|---|---|
| pAR3924 | pBR322 | Ampicillin | Gene 9 Scaffolding Protein | ϕ10 |
| pAR5403 | pBR322 | Ampicillin | Gene 10A capsid protein | ϕ10 |
| pAR5453 | pACYC184 | Chloramphenicol | Gene 10A capsid protein | ϕ10 |
| pAR5615 lacUV5 | pBR322 | Ampicillin | Gene 10A | lacI- |

As indicated above, peptides and proteins were cloned within the polylinker following 10B amino acid 348. Double stranded oligos were cloned between BamHI and EcoRI sites of the vector. Restriction fragments were cloned between similar sites in the vector, except that NdeI to EcoRI adaptors (5'-TATGCGAATTCGCA) were added to NdeI ends. Clones were detected by restriction analysis, either on DNA of purified phage, or on PCR DNAs made from plaques, either individually or in batches. The DNA of phage displaying peptides was sequenced through the insert. The reading frame of the T7 RNA polymerase fusion was confirmed in pAR5459. In Table 4, a+ in the "sequenced column" (SEQ) indicates that the DNA of phage displaying peptides was sequenced through the insert. The reading frame of the T7 RNA polymerase fusion was confirmed in pAR5459. A+ in the "display column" (DSP) indicates that phage were positive in either a binding or enzymatic test for display.

TABLE 4

| | Phage Display | | | |
|---|---|---|---|---|
| Phage Display | Host | Source | SEQ | DSP |
| PD1/RGD | BL21 | ds oligo[e] | + | + |
| PD1/streptavidin | BL21/pAR5403[f] | ds oligo[g] | + | + |
| PD1/HSV epitope | BL21 | Homologous recombination of | + | + |

TABLE 4-continued

Phage Display

| Phage Display | Host | Source | SEQ | DSP |
|---|---|---|---|---|
| | | D104, Δ3.8, Δϕ10-10AB with pAR5400 | | |
| PD1/thrombin site | BL21 | ds oligo[h] | + | + |
| PD1/HSV epitope-His | BL21 | Homologous recombination of D104, Δ3.8, Δϕ10-10AB with pAR5401 | + | + |
| PD2/HSV epitope | BL21/pAR5403 | BamHI-EcoRI fragment of pAR5265 | + | + |
| PD2/T7 endonuclease | BL21/pAR5403 | NdeI-HindIII fragment of pAR3660 | − | + |
| PD2/T7 ssDNA binding protein | BL21/pAR5403 | NdeI-HindIII fragment of pAR6050 | − | nd |
| PD2/T7 DNA polymerase | BL26/pAR5615 | NdeI-HindIII fragment of pAR2751 | − | − |
| PD3/T7 RNA polymerase | BL26/pAR5615 | BssHI-HindIII fragment of pAR5459 | + | + |
| PD2/β-gal- | | | | |
| 71[i] | BL21/pAR5403 | BamHI-EcoRI, pAR5154 | − | + |
| 271 | " | BamHI-EcoRI, pAR5155 | − | + |
| 431 | " | BamHI-EcoRI, pAR5160 | − | + |
| 691 | " | BamHI-EcoRI, pAR5158 | − | + |
| PD3/β-gal-833 | BL26/pAR5615 | BamHI-EcoRI, pAR5159 | − | + |
| PD3/β-galactosidase | BL26/pAR5615 | SacI-HindIII fragment of pAR5134 inserted between SacI and HindIII sites of PD3/β-gal-833 | − | + |

[e] 5'-GATCCGGCGATTCGTGGCGATACCTTTGCATAAGGCCGCTAAGCACCGCTATGGAAACG-TATTCTTAA-5'

[f] PD1/strep tag grows poorly on BL21, but is maintained well on BL21/10A-5403.

[g] 5'-GATCCGAGCGCTTGGCGTCACCCGCAGTTCGGTGGTTAATGGCTCGCGAACCGCA-GTGGGCGTCAAGCCACCAATTACTTAA-5'

[h] 5'-GATCTGGTTCCACGCGGCAGTGCGGATCCGATATCGACCAAGGTGCGCCGTCACGCCTAG-GCTATAGCTTAA-5'

[i] The number suffix refers to the number of β-gal amino acids in the fusion, starting at amino acid 9. The β-gal fragments lack a translation terminator. Termination is determined by the reading frame at the EcoRI site, which should be GAA for all of the β-fragments except β-gal-833, which should be AAT. The GAA frame terminates at the 3rd terminator in the polylinker and adds 16 amino acids to the protein; the AAT frame terminates at the 1st terminator and adds 13 amino acids.

The actual sequences of the displayed peptides are set forth below. In the following sequences, the coding sequence of functional peptide are underlined.

1. RGD peptide from adenovirus penton protein (Bai et al., J. Virol. 67: 5198 (1993)).

```
    348                                                  358
Met Leu Gly Asp Pro Ala Ile Arg Gly Asp Thr Phe Ala
---ATG CTC GGG GAT CCG GCG ATT CGT GGC GAT ACC TTT GCA TAA
```

2. Streptavidin tag (Schmidt and Skerra, Protein Eng. 6: 109 (1993)).

```
    348                                                      360
Met Leu Gly Asp Pro Ser Ala Trp Arg His Pro Gln Phe Gly Gly
---ATG CTC GGG GAT CCG AGC GCT TGG CGT CAC CCG CAG TTC GGT GGT TAA
```

3. Herpes Simplex Virus (HSV) glycoprotein D epitope (Isola et al., J. Virol. 63: 2325 (1989)).

```
    348                                                              362
Met Leu Gly Asp Pro Ser Gln Pro Glu Leu Ala Pro Glu Asp Pro Glu Asp
---ATG CTC GGG GAT CCG AGC CAG CCA GAA CTC GCC CCG GAA GAC CCC GAG Gat TAA
```

4. Thrombin cleavage site

```
    348                         ↓
Met Leu Gly Asp Leu Val Pro Arg Gly Ser Ala Asp Pro Ile Ser Asn Ser Ser
--ATG CTC GGG GAT CTG GTT CCA CGC GGC AGT GCG GAT CCG ATA TCG AAT TCG AGC
                                                           371
Ser Val Asp Lys Leu Ala Ala Ala Leu Glu
TCC GTC GAC AAG CTT GCG GCC GCA CTC GAG TAA
```

5. HSV epitope + His Tag

-continued

```
                                                    348
    Met Leu Gly Asp Pro Asn Ser Ser Ser Val Asp Lys Leu Ala Ala Ala Leu Glu
----ATG CTC GGG GAT CCG AAT TCG AGC TCC GTC GAC AAG CTT GCG GCC GCA CTC GAG

Ile Lys Arg Ala Ser Gln Pro Glu Leu Ala Pro Glu Asp Pro Glu Asp Val Glu His
    ATC AAA CGG GCT AGC CAG CCA GAA CTC GCC CCG GAA GAC CCC GAG GAT GTC GAG CAC
                                                                              387
    His His His His His
    CAC CAC CAC CAC CAC TGA
```

The displayed peptides were then tested for integrity. The ability of PD1/RGD phage to bind to A549 cells (Bai et al., *J. Virol.* 67: 5198–5205 (1993)) was determined using cells in solution. PD1/RGD lysate or control PD1 lysate were incubated for 1 hr at 37° C. with $3 \times 10^5$ A549 cells at a ratio of 1000 phage per cell in a final volume of 1 ml Hanks BSS 2% BSA buffer. After centrifugation and several washes, phage were released from cells suspended in buffer by adding SDS to 1%. The sample was sonicated to reduce viscosity and titered for infective phage. About 2.5% of RGD phage were recovered compared to 0.05% of the control phage. This represents about 25 RGD phage bound per cell, well below the estimated number of RGD receptors. However, binding was competitively inhibited by free RGD peptide but not by a mock peptide, indicating that the binding was specific for the RGD receptor.

The ability of PD1/strep tag phage to bind to streptavidin paramagnetic beads (Promega) was tested using the protocol suggested by the manufacturer. 50 µl of PD1/strep tag lysate ($8.7 \times 10^{10}$ infective phage/ml) or control PD1 lysate ($5.2 \times 10^{10}$) were mixed with 75 µl beads in an Eppendorf centrifuge tube. After magnetic settling and several washes, phage were eluted from the beads with 1 mM biotin and titered. About 47% of the infective PD1/strep tag phage were recovered but less than 0.1% of the control phage. The PD1/strep tag phage had been grown on BL21/10A-5403, so the capsid protein was a mixture of 10A and capsid/strep tag fusion protein. Western analysis with monoclonal antibody to the strep tag indicated that perhaps ⅓ of the capsid protein was fusion protein, the equivalent of 140 copies of strep tag per phage.

The ability of PD1/HSV epitope and PD2/HSV epitope phage to bind to a mouse monoclonal antibody to the epitope (Novagen) or to be selected from a pool of non-epitope phage was tested in microtiter dish assays (bio-panning). Briefly, 50 µl lysate was allowed to bind in a 200 µl microtiter dish well (Dynatech Immulon) that had been coated with antibody (40 µg/ml). After a series of washes, phage were recovered in buffer containing 1% SDS and titered and, in the selection experiments, used to grow new lysates.

Binding efficiencies (recovered infective phage) were: PD1/HSV, 65%; PD2/HSV, 1%; PD1, 0.0004%; PD2, 0.01%. The results of selection experiments where the ratio of epitope to non-epitope phage was varied from 1:1 to $1:10^6$ are shown below. For example, when initially present in $1:10^6$ PD1/HSV phage made up about 10% of the population after one round of selection (a $10^5$-fold enrichment), and PD2 phage were about 25% of the population after three rounds of selection (50- to 100-fold enrichment per round). The difference in the efficiency of binding and selection of the PD1 and PD2 display phage represents the difference in copy number of the epitope: 415 per phage for PD1/HSV and about 1 per every 2 phage for PD2/HSV.

TABLE 5

Selection of PD1/HSV Epitope Phage

| PD1/HSV:PD1 | % PD1/HSV | Rounds of Selection |
|---|---|---|
| 1:1 | 100 | 1 |
| $1:10^2$ | 98 | 1 |
| $1:10^4$ | 58 | 1 |
| $1:10^6$ | 10 | 1 |

TABLE 6

Selection of PD2/HSV Epitope Phage

| PD2/HSV:PD2 | % PD2/HSV | Rounds of Selection |
|---|---|---|
| 1:1 | 92 | 1 |
| $1:10^2$ | 48 | 1 |
| $1:10^4$ | 54 | 2 |
| $1:10^6$ | 26 | 3 |

The accessibility of thrombin cleavage sites displayed from PD1 was tested by treatment of purified phage with thrombin followed by analysis of phage structural proteins by gel electrophoresis. PD1/thrombin site or control PD1 phage were filter dialyzed against phage dilution buffer (0.2M NaCl, 2 mM Tris-HCl, pH8, 0.2 mM EDTA) and incubated for 1 hr at 37° C. in thrombin buffer (150 mM NaCl, 20 mM Tris-HCl, pH 8, 2.5 mM $CaCl_2$) in the presence of various amounts of thrombin (Novagen) in a final vol of 10 µl and phage concentration $A_{260}=12$. The treated phage were heated for 2 min in a boiling water bath in the presence of cracking buffer and analyzed on an SDS-polyacrylamide gel that had a 10–20% gradient of polyacrylamide with a 5% stack, essentially as described (Studier, *J. Mol. Biol.* 79: 237 (1973)).

Sufficient levels of thrombin cleaved most or all of the thrombin sites (415/phage), reducing the capsid/thrombin site fusion protein (373 aa) to a smaller form consistent with the expected size of cleaved protein (353 aa). The control PD1 capsid protein (363 amino acids) was unaffected by thrombin. The thrombin site phage retained essentially full infectivity after thrombin treatment, suggesting that the thrombin sites were displayed on the outside of the capsid.

The ability of PD1 phage displaying the His tag to bind to a nickel His-bind column (Novagen) was tested using the protocol suggested by the manufacturer. 4 ml of PD1/HSV-His tag or PD1/HSV (no His tag) or PD1 lysate (each about $7 \times 10^{10}$ infective phage/ml) were loaded on 2.5 ml His-bind columns. After several washes, phage were released by stripping the column of nickel using EDTA and titered for recovery. About 45% of the His tag phage were recovered compared to less than 0.1% of the PD1/HSV or PD1 phage. The bulk of the control phage was found in the flow through, representing material that did not bind at all to the column.

Following successful demonstration of peptide display, larger protein display was undertaken using the PD2 and PD3 derivatives. The endpoints of the sequences of the displayed proteins are shown below.

```
                                aaᵃ
                                bpᵇ
         10B------------------ linker-protein
         aa 1          aa 348

1         149
                                                   10,257    10,704
                                                     |         |
  PD2/T7 endonuclease    10B³⁴⁸-GAT CCG AAT TCG CAT ATG----------TAA
       (gene 3)

1         232
                                                   9,158     9,854
                                                     |         |
  PD2/T7 ssDNA binding protein  10B³⁴⁸-GAT CCG AAT TCG CAT ATG----------TAG
       (gene 2.5)

1         704
                                                   14,353    16,465
                                                     |         |
  PD2/T7 DNA polymerase   10B³⁴⁸-GAT CCG AAT TCG CAT ATG----------TGA
       (gene 5)

11         883
                                         3,201      5,820
                                           |          |
  PD2/T7 RNA polymerase   10B³⁴⁸-GAT CCG GAA TTC----------TAA
       (gene 1)

9        1,023
                                    1,311      4,356
                                      |          |
  PD2/β-galactosidase    10B³⁴⁸-GAT CCC GTC----------TAA
       (lacZ)

1         253
                                      2         758
                                      |          |
  PD2/anti-digoxin       10B³⁴⁸-GAT CCG AAT----------GCC GCA GCA CTC GAG
  TAA
       (scFv anti-dig)
```

ᵃEnd-points of amino acid sequence.
ᵇEnd-points of DNA sequence.
T7: Dunn and Studier, J. Mol. Biol. 166: 477–535 (1983); GenBank phg T7CG
LacZ: GenBank bct ECOLAC
Anti-dig: Becton Dickinson & Co.

All enzymes displayed by phage were fused at their N-terminus to the capsid protein, and activities were measured using phage purified by PEG precipitation followed by centrifugation through CsCl step gradients. Prior to the assay, the phage were filter-dialyzed against phage dilution buffer (0.2 mM NaCl, 2 mM Tris-HCl, pH 8, 0.2 mM EDTA). To be scored as having enzymatic activity, the displayed enzyme was required to retain activity when fused to the capsid. Survival of this activity through the purification procedure was also required. T7 endonuclease and E. coli β-galactosidase phage both showed activity. T7 RNA polymerase phage were not active but were positive in dot-blot Westerns with polyclonal antibody, suggesting that at least some part(s) of the protein were in a conformation that could be recognized by the antibody. T7 DNA polymerase phage did not show enzymatic activity, and antibody for any kind of binding test was unavailable. Phage displaying the T7 ssDNA binding protein have not yet been tested for binding to DNA.

To determine T7 endonuclease (gene 3) activity, the activity of purified PD2 phage displaying the T7 endonuclease (PD2/endo) was compared to the activity of purified endonuclease (de Massy et al., J. Mol. Biol. 193: 359 (1987)). Approximately equimolar amounts of endonuclease, PD2/endo, or PD2 were added to the substrate ssM13 DNA (1.5 μg) in the presence of endonuclease buffer (50 mM Tris, pH 8, 10 mM $MgSO_4$, 1 mM DTT, BSA (50 μg/ml)) in a final vol of 55 μl, and a time course of activity was analyzed by agarose gel electrophoresis. About 0.4 ng endonuclease were used per assay and a similar amount of PD2/endo, assuming 1 copy of endonuclease per every 2 phage. 10 μl samples were taken out after 5, 10, 20, 30 or 60 min incubation at 37° C., and the samples were heated at 70° C. for 5 min in the presence of dye-EDTA loading buffer. The total sample was loaded on a 1% agarose gel and DNAs were visualized by staining the gel with ethidium bromide.

Purified endonuclease and PD2/endo showed very similar patterns of activity, as judged by the rate of disappearance of ssM13 DNA and appearance of a characteristic streak of lower molecular weight digestion products. The control PD2 phage has no effect on the M13 DNA. The PD2/endo and PD2 control phage retained essentially full infectivity after the incubation, showing that it is the intact phage that has the endonuclease activity.

To determine E. coli β-galactosidase activity, the activity of purified PD3 phage displaying β-galactosidase (PD3/β-gal) was compared to the activity of purified β-galactosidase in a slightly modified Miller assay (Miller, J. H. (1972), Experiments in Molecular Genetics, Cold Spring Harbor Laboratory, Cold Spring Harbor, N.Y.). The phage were purified after growth on a lac⁻ host (BL26/pAR5615). Aliquots of PD3/β-gal or control PD3 phage ($A_{260}=6$) or of purified β-gal (Boehringer-Mannheim, 600–950 units/mg) in assay buffer (1×M9 salts, 1 mM $MgSO_4$, 35 mM β-mercaptoethanol) were incubated for 2 hr at 37° C. in the presence of the substrate ONPG (0.5 mg/ml) in a final vol of 0.8 ml, and the amount of activity was measured colorimetrically at $A_{420}$. Table 7, below, shows the results of these experiments. The PD3/β-gal phage had β-gal activity proportional to the amount of phage added, but the amount of activity was equivalent to about 1 copy of β-gal per 250 phage, very much lower than the measured physical copy number (1 per 3 phage). Since β-gal requires tetramerization for activity, the low activity may represent the frequency of active tetramers incorporated in the capsid, though other explanations are also possible, e.g. the β-gal activity may represent a tetramer of which at least some monomer subunits are bound to the capsid but are not an integral part of the capsid structure. Both the PD3/β-gal and the control PD3 phage showed about 20–30% loss in infectivity after the 2 hr incubation.

TABLE 7

| | β-galactosidase activity | | |
|---|---|---|---|
| | PD3/β-gal | PD3 | | β-gal |
| 50 µl | .1392 | .0040 | 1 ng | .4137 |
| 20 µl | .0666 | .0063 | 0.2 ng | .0936 |
| 10 µl | .0359 | .0020 | 0.04 ng | .0107 |
| 5 µl | .0220 | .0048 | 0.008 ng | .0039 |

Purified PD2/β-gal-71, -271, -431, and -691 and PD3/β-gal-833 phage were all positive in dot blot Westerns with polyclonal rabbit anti-β-gal (Cappel).

Reaction of purified PD3 phage displaying T7 RNA polymerase and of purified T7 RNA polymerase with rabbit polyclonal antibody to T7 RNA polymerase were compared in dot blot Westerns using PVDF paper and a Bio-Rad color development kit for detecting alkaline phosphatase-labeled goat anti-rabbit antibody. The reaction of both phage and purified T7 RNA polymerase were approximately proportional to the amount applied to the paper, and control PD3 phage showed no reaction at all. The color intensity of PD3/T7 RNA polymerase phage represented the equivalent of about 1 T7 RNA polymerase per 10 phage, rather close to the 1 per 7 phage measured using gel Westerns.

PD2 phage displaying the single-chain Fv anti-digoxin were tested for the ability to bind to DNA labeled with digoxigenin in a bio-panning assay. T7 DNA labeled with dig-dUTP (Boehringer-Mannheim) was bound to monoclonal anti-digoxigenin (Boehringer-Mannheim) coating a microtiter dish well (Dynatech Immulon, 200 µl wells). The well was first incubated with antibody (10 µg/ml), washed several times, and then incubated with DNA (300 ng/ml), either unlabeled or labeled with digoxigenin followed by several washes. PD2/anti-dig or control PD2 lysate (each at $3 \times 10^{10}$ infective phage/ml) were then incubated in the well for 1 hr at RT. After removing the lysate and several washes, bound phage were eluted in a buffer containing 1% SDS and titered. About 0.4% of the anti-dig phage was recovered when dig-labeled DNA was used compared to 0.003% of the control phage or 0.005% if unlabeled DNA was used.

TABLE 8

| Copy Number | |
|---|---|
| Peptide or Protein | Copy Number |
| HSV epitope | 1 per 2 phage |
| ssDNA binding protein | 1 per 3 phage |
| β-galactosidase | 1 per 5 phage |
| T7 RNA polymerase | 1 per 7 phage |

The copy number displayed from PD2 has been measured in 4 cases using standard gel Western analysis. The results are summarized in the Table 8, shown above. To determine copy number, phage particle proteins were precipitated in 10% TCA, washed with 90% acetone, and suspended in cracking buffer and heated for 2 min in a boiling water bath prior to analysis on an SDS-12% polyacrylamide gel using a Bio-Rad Mini-Protean II Dual Slab Gel system. Transfer to PVDC paper was done in the cold at 70 volt for 90 min in a Bio-Rad Mini Trans-Blot Electrophoretic Transfer Cell. In the case of HSV, the epitope was visualized using mouse monoclonal antibody to the epitope (Novagen). The copy number of the displayed proteins was determined in a similar way, except that comparison was to purified protein.

In general, packaging extracts were made under conditions where the DNA of the infecting phage does not replicate, so that there is little T7 DNA in the extract to compete with the DNA to be packaged. Replication is prevented by using BL24, a host that lacks thioredoxin, a necessary component of T7 DNA polymerase. Since packaging extracts are also recombination proficient, they are made with a deletion phage that cannot recombine with the vector DNAs to form viable phage. This eliminates one source of background in cloning. The proteins that the deletion phage lacks (genes 9 and 10) are provided from plasmids in the host. Except for T7 DNA polymerase, the extracts contain all T7 proteins required for T7 growth, including those for DNA packaging and viral assembly. T7 DNA polymerase is needed for the formation of concatemers of T7 DNA, a requirement for efficient packaging. It should be sufficient to simply add thioredoxin to form T7 DNA polymerase with the T7 gene 5 protein present in the extract, but it was determined that packaging efficiencies are somewhat higher if complete T7 DNA polymerase is added.

Packaging phage PDpkg=Δ9–10B,D104,Δ3.8

Host for growth: BL21/pAR3924,pAR5453 $Amp^R Cam^R$

Host for making extracts: BL24/pAR3924,pAR5453 $Amp^R Cam^R$

Table 9 summarizes the plasmids employed herein. The plasmids which encode only 10A or only 10B were created by introducing changes in the nucleotide sequence that remove the frameshift site (10A only) or that place 10B in a single reading frame (10B only). Additional changes were made in the 10B only gene in the region where 10A and 10B reading frames diverge in order to reduce homologous recombination between the genes when in the same cell. The original 10A only clone (pAR5116) did not contain the G to A change in the last codon. This was changed in other 10A complementing plasmids to interrupt an 11 bp stretch of homology between 10A and the polylinker in the vectors.

```
                                 340 341       344
            E   A   A   G   A   V   V   F   K   V   E
WT 10AB  ---GAA GCT GCT GGT GCA GTG GTT TTC AAA GTG GAG TAA TGC TG- ---
                                     ↓   ↓           ↓
10A only                             C   T           A E   A   A   G   A   V   V   F   Q   S   G   V   M   L
10B frameshift GAA GCT GCT GGT GCA GTG GTT TTT CAA AGT GGA GTA ATG CTG ---
             ↓   ↓   ↓   ↓   ↓   ↓   ↓   ↓  ↓↓↓   ↓   ↓       ↓
10B only ---GAA GCT GCA GGA GCT GTC GTA TTC CAG TCA GGT GTG ATG CTC ---
```

TABLE 9

Plasmids

| Plasmid[a] | Elements[b] | DNA insert (bp)[c] |
|---|---|---|
| pAR2197 | φ10-s10-BamHI-β-gal (aa 9-1023) | ECOLAC 1311-4373[d] |
| pAR2751 | φ10-s10-5-BamHI | 14,353–16,706 |
| pAR2802 | φ9-9-φ10-10AB-Tφ | 21,403–24,273 |
| pAR3625 | φ10-10AB-Tφ | 22,881–24,273 |
| pAR3660 | φ10-s10-3-BamHI | 10,257–10,723 |
| pAR3924 | φ10-s10-9 | 21,950–22,872 |
| pAR5037 | lacI-lacUV5-XbaI-BamHI | ECOLAC 1-1274[d] |
| pAR5116 | φ10-10A-SpeI | 22,881–24,004 |
| pAR5120 | φ9-9-(Δφ10-10AB)-SpeI-Tφ | 21,403–22,872 + 24,169–24,273 |
| pAR5128 | φ10-10A-SpeI-Tφ | 22,881–24,004 + 24,169–24,273 |
| pAR5129 | φ9-9-φ10-10A-SpeI-Tφ | 21,403–24,004 + 24,169–24,273 |
| pAR5130 | φ10-10B³⁴⁸-BamHI | 22,881–24,012 |
| pAR5134 | φ10-10B³⁴⁸-β-gal | 22,881–24,012 + ECOLAC 1311-4373[d] |
| pAR5135 | φ10-10B-SpeI | 22,881–24,162 |
| pAR5154 | φ10-10B³⁴⁸-β-gal-71 | ECOLAC 1311–1529 |
| pAR5155 | φ10-10B³⁴⁸-β-gal-271 | ECOLAC 1311–2128 |
| pAR5158 | φ10-10B³⁴⁸-β-gal-691 | ECOLAC 1311–3388 |
| pAR5159 | φ10-10B³⁴⁸-β-gal-691 | ECOLAC 1311–3813 |
| pAR5160 | φ10-10B³⁴⁸-β-gal-431 | ECOLAC 1311–2608 |
| pAR5265 | φ10-10B³⁴⁸-HSV epitope-SpeI | 22,881–24,012 + HSV |
| pAR5266 | φ10-10B³⁴⁸-polylinker-HSV epitope-His tag | 22,881–24,012 + polylinker-HSV-His |
| pAR5365 | φ10-(Δs10)-10B | 22,881–22,930 + 22,967–24,162 |
| pAR5396 | φ10-10B³⁴⁸-polylinker-TAA-SpeI | 22,881–24,012 + polylinker |
| pAR5400 | φ9-9-φ10-10B³⁴⁸-HSV epitope-Spe-Tφ | 21,403–24,012 + HSV + 24,169–24,273 |
| pAR5401 | φ9-9-φ10-10B³⁴⁸-HSV epitope-His tag-Spe-Tφ | 21,403-24,012 + polylinker-HSV-His + 24,169–24,273 |
| pAR5402 | φ9-9-φ10-10B³⁴⁸-polylinker-TAA-SpeI-Tφ | 21,403–24,012 + polylinker + 24,169–24,273 |
| pAR5403 | φ10-10A-EcoRI | 22,881–24,004 |
| pAR5416 | 8-φ9-SpeI-EcoRI | 20,240–21,871 |
| pAR5426 | φ9-9-Spe/Xba-(Δφ10-s10)-10B | 22,881–22,872 + 22,967–24,162 |
| pAR5452 | 8-φ9-(Δ9-10AB)-SpeI-Tφ | 20,240–21,871 + 24,169–24,273 |
| pAR5453 | φ10-10A | 22,881–24,004 |
| pAR5459 | lac-10B³⁴⁸-BamHI-EcoRI-1 (aa 11–883) | 3,201–5,841 |
| pAR5600 | φ10-10B³⁴⁸-EcoRI-scFV anti-dig-NotI-HSV epitope-His tag | Anti-dig 2-758[e] + HSV epitope + His tag |
| pAR5615 | lac-10A | 22,881–24,004 |
| pAR6050 | BamHI-NdeI-2.5-HindIII | 9158–9855 |

[a]All plasmids are based on pBR322 (Amp^R) except pAR5453, which is based on pACYC184 (Cam^R).
[b]φ10 and s10 refer to the T7 promoter and translation initiation site found upstream of T7 gene 10 and used to control T7 RNA polymerase-directed expression from pET vectors (Studier et al., Methods in Enzymology, 185, 60–89 (1990)). If both signals are listed, the T7 or lacZ DNA was cloned in the equivalent of pET-1b. Lac = lacI-lacUV5. Signals and DNA are inserted in the counterclockwise orientation between the BamHI and either the BamHI, HindIII, or EcoRI sites of the plasmid. T7 genes are listed by number alone, e.g., 9 = gene 9. 10A and 10B refer to the 10A only and 10B only genes and 10B³⁴⁸ is the 10B only gene to aa 348.
[c]Unless otherwise marked, the end-points are of T7 DNA (Dunn and Studier, J. Mol. Biol. 166, 477–535 (1983)) inserted in the vector. The new junctions created in the plasmid and any nucleotide alterations in the T7 DNA are defined by the cloning manipulations.
[d]Lac DNA sequence is from GenBank (ECOLAC).
[e]The original single chain Fv anti-digoxin clone was made by Becton Dickinson & Co.

The description of the construction of several plasmids used in connection with the experiments described above follows.

pAR2197. φ10-s10-β-gal clone: The BamHI fragment carrying βgal aa 9–1023 from pMC1871 (Casadaban et al., Methods in Enzymology, 100, 293–308 (1983)) was inserted in the BamHI site of pET-1b.

pAR2751. T7 DNA polymerase, gene 5: A Sau3A-AvaII fragment of T7 DNA was inserted between the NdeI and BamHI sites of pET-1b, using NdeI and BamHI linkers.

pAR2802. φ9-9-φ10-10AB-Tφ: Contains an AccI-PvuII fragment of T7 DNA inserted in the BamHI site of pBR322 with BamHI linkers.

pAR3625. φ10-10AB-Tφ: Contains a TaqI-PvuII fragment of T7 DNA inserted in the BamHI site of pBR322 with BamHI linkers.

pAR3660. T7 endonuclease, gene 3: A HinfI-DraI fragment of T7 DNA was inserted between the NdeI and BamHI sites of pET-1b using NdeI and BamHI linkers.

pAR3924. φ10-s10-9 clone: A PCR DNA containing T7 gene 9 made from a T7 DNA template was inserted between the NdeI and EcoRI sites of pET-1b. The PCR primers were: upstream primer 5'-CGCGGATCCAT/ATGGCTGAATCTAATG, and downstream primer 5'-GATTCGAACTTCT/AAGCTAGCGAATTCCCG (complement).

pAR5116. 10A only clone: A ds oligo to remove the frameshift site and terminate the clone at the 10A termination codon was inserted between AlwNI and EcoRI sites of the 10AB clone, pAR3625, to create pAR5116.

ds oligo  5'-CTGCTGGTGCAGTGGTCTTTAAAGTGGAGTAACTAGTG
          TTCGACGACCACGTCACCAGAAATTTCACCTCATTGATCACTTAA-5' pAR5120, plasmid to create Δφ10-10AB phage: A ds oligo to create the deletion and an SpeI site and Tφ after the gene 9 termination codon was inserted between BstBI and StyI sites of pAR2802, creating pAR5120.

ds oligo  5'-CGAACTTCTAACTAGTTAACCC
             TTGAAGATTGATCAATTGGGGAAC-5' pAR5129, plasmid used in PD1 construction: The SpeI-PstI fragment of pAR5120 carrying Tφ was inserted between the SpeI and EcoRI sites of pAR5116, creating pAR5128 with 10A only followed by an SpeI site and Tφ. The XbaI-PstI fragment of pAR5128 carrying 10A-Tφ replaced the analogous fragment of pAR2802, to create pAR5129.

pAR5130, 10B$^{348}$ clone: A ds oligo to create 10B to aa 348 in a single reading frame ending with AvaI and BamHI sites, with conservative changes to minimize recombination with the 10A only gene, was inserted between AlwNI and BamHI sites of pAR3625, creating pAR5130.

pAR5400, plasmid for making PD1/HSV epitope: Acc65I-SpeI fragment of pAR5129 replaced with Acc65I-SpeI fragment of pAR5265, which extends the sequence upstream of 10B through the natural gene 9 sequence and downstream through Tφ.

pAR5401, plasmid for making PD1/HSV-His tag: Acc65I-SpeI fragment of pAR5129 replaced with Acc65I-SpeI fragment of pAR5266, which extends the sequence upstream of 10B through the natural gene 9 sequence and downstream through Tφ.

pAR5403, φ10-10A: A ds oligo introducing the change in the final codon of the 10A only gene was inserted between AlwNI and EcoRI sites of pAR5116.

oligo  5'-CTGCTGGTGCAGTGGTCTTTAAAGTGGAATAAG
          TTCGACGACCACGTCACCAGAAATTTCACCTTATTCTTAA-5' pAR5416, gene 8-φ9 clone: A PCR DNA carrying gene 8-φ9 followed by an SpeI site was made using a T7 DNA template and inserted between BamHI and EcoRI sites of pBR322 (upstream primer 5'-CGGGATCCAT/ATGGCTGAGAAACGA, and downstream primer 5'-CTCACTATAGGGAG/ACTAGTGAATTCGC (complement)).

ds oligo  5'-CTGCAGGAGCTGTCGTATTCCAGTCAGGTGTGATGCTCGGG
             TTCGACGTCCTCGACAGCATAAGGTCAGTCCACACTACGAGCCCCTAG-5' pAR5135, 10B only clone: A PCR DNA to attach the remaining codons of 10B to the 10B$^{348}$ clone was made using T7 DNA as template. The PCR DNA introduced a SacII site near the 3' end of 10B and an SpeI site after the 10B termination codon, and was inserted between BamHI and EcoRI sites of pAR5130, creating pAR5135 (upstream primer 5'-CGGGATCCTC/GGGGTGGCCTCAACG; downstream primer 5'-GGCTGCTGCCACCGCGGAGCAATAACTAG/TGAATTCGC (complement)).

pAR5265, 10B$^{348}$/HSV epitope: A ds oligo containing the HSV epitope followed by an SpeI site was inserted between BamHI and EcoRI sites of pAR5130, creating pAR5265.

pAR5452, 8-φ9-(Δ9-10AB)-SpeI-Tφ, plasmid for making PDpkg: An SpeI-PstI fragment of pAR5416 was replaced with the SpeI-PstI fragment of pAR5120 carrying Tφ.

pAR5453, φ10-10A: An AvaI-EcoRI fragment of pAR5403 carrying φ10-10A was inserted between AvaI and HindIII sites of pACYC184. The EcoRI and HindIII sites were filled in before cloning.

pAR5459, T7 RNA polymerase, gene 1: An EcoRI-BamHI fragment of pAR3105 carrying gene 1 (Dunn et al., Gene 68, 259–266 (1988)) was inserted in the BamHI site of pAR5251 (lac-10B$^{348}$-BamHI) using an EcoRI to BamHI converter.

pAR5600, φ10-10B$^{348}$-anti-dig-HSV epitope-His tag: An EcoRI-NotI fragment carrying the single-chain Fv antioligo  5'-GATCCGAGCCAGCCAGAACTCGCCCCGGAAGACCCCGAGGATTAACTAGTG
          GCTCGGTCGGTCTTGAGCGGGGCCTTCTGGGGCTCCTAATTGATCACTTAA-5' pAR5266, 10B$^{348}$/HSV epitope-His tag fusion: A PCR DNA with the polylinker and HSV/His sequence followed by a TGA termination codon and an SpeI site was made using pET-22b as a template. The PCR DNA was inserted between the BamHI and EcoRI sites of pAR5130, where the EcoRI site was filled in followed by 3-dTTP addition, to enable T-A tail cloning at the 3' end. The cloning is predicted to eliminate the EcoRI site creating the sequence TGAACTAGTAAATTC where the TGA is the termination codon of the fusion gene.

digoxin gene (Becton Dickinson & Co.) was inserted between these sites in the polylinker of pAR5266.

pAR6050, T7 ssDNA binding protein, gene 2.5: A DNA carrying gene 2.5 was made by PCR using T7 DNA as a template and inserted between the BamHI and HindIII sites of pBR322. The PCR DNA established an NdeI site at the 2.5 initiation codon (upstream primer 5'-CGCGGATCCATATGGCTAAGAAGATT, downstream primer 5'-GACGGAGACTTCTAGAAGCTTCGGC (complement)).

We claim:

1. A bacteriophage T7 display vector comprising DNA encoding at least residues 1 through 341 of the bacteriophage T7 capsid protein followed by a cloning site for the in-frame insertion of a foreign DNA sequence encoding a peptide or protein of interest.

2. The bacteriophage T7 display vector of claim 1 further comprising amino acid residues 342–348 of the 10B form of the bacteriophage T7 capsid protein.

3. The bacteriophage T7 display vector of claim 1, further comprising wild-type T7 capsid protein regulatory signals.

4. The bacteriophage T7 display vector of claim 3, wherein the wild-type capsid protein regulatory signals comprise promoter and translation initiation signals.

5. The bacteriophage T7 display vector of claim 4, wherein the promoter is the $\phi10$ promoter and the translation initiation signal is the s10 translation initiation signal.

6. The bacteriophage T7 display vector of claim 5, further comprising the wild type T$\phi$ terminator.

7. The bacteriophage T7 display vector of claim 2 which lacks wild-type capsid protein promoter and translation initiation signals.

8. A cell containing a bacteriophage T7 display vector comprising DNA encoding at least residues 1 through 341 of the bacteriophage T7 capsid protein followed by a cloning site for the in-frame insertion of a foreign DNA sequence encoding a peptide or protein of interest.

9. The cell of claim 8 wherein the bacteriophage T7 display vector further comprises amino acid residues 342–348 of the 10B form of the bacteriophage T7 capsid protein.

10. The cell of claim 8, further comprising wild-type T7 capsid protein regulatory signals.

11. The cell of claim 10, wherein the wild-type capsid protein regulatory signals comprise promoter and translation initiation signals.

12. The cell of claim 11, wherein the promoter is the $\phi10$ promoter and the translation initiation signal is the s10 translation initiation signal.

13. The cell of claim 12, further comprising the wild type T$\phi$ terminator.

14. The cell of claim 8 which lacks wild-type capsid protein promoter and translation initiation signals.

15. A viral lysate containing assembled bacteriophage T7 particles, the assembled bacteriophage T7 particles containing a fusion protein comprising at least residues 1 through 341 of the bacteriophage T7 capsid protein fused to a peptide or protein of interest.

16. The viral lysate of claim 15 wherein the assembled bacteriophage T7 particles further comprise amino acid residues 342–348 of the 10B form of the bacteriophage T7 capsid protein.

17. A bacteriophage T3 display vector comprising DNA encoding at least residues 1 through 341 of the bacteriophage T7 capsid protein followed by a cloning site for the in-frame insertion of a foreign DNA sequence encoding a peptide or protein of interest.

18. The bacteriophage T3 display vector of claim 17 further comprising amino acid residues 342–348 of the 10B form of the bacteriophage T7 capsid protein.

* * * * *